United States Patent [19]

Kang et al.

[11] Patent Number: 4,535,153
[45] Date of Patent: Aug. 13, 1985

[54] HETEROPOLYSACCHARIDE S-88

[75] Inventors: Kenneth S. Kang, LaJolla; George T. Veeder, San Diego, both of Calif.

[73] Assignee: Merck & Co., Inc., Rahway, N.J.

[21] Appl. No.: 587,736

[22] Filed: Mar. 8, 1984

Related U.S. Application Data

[63] Continuation of Ser. No. 355,934, Mar. 8, 1982, abandoned, which is a continuation-in-part of Ser. No. 256,625, Apr. 23, 1981, abandoned, which is a continuation-in-part of Ser. No. 73,575, Sep. 7, 1979, abandoned.

[51] Int. Cl.$^3$ .................. C08B 37/00; C12P 19/06
[52] U.S. Cl. .................. 536/123; 536/114; 536/1.1; 435/104
[58] Field of Search ............... 536/1.1, 114, 119, 123

[56] References Cited

U.S. PATENT DOCUMENTS

| | | | |
|---|---|---|---|
| 3,960,832 | 6/1976 | Kang et al. | 536/123 |
| 4,211,774 | 7/1980 | Kang et al. | 536/123 |
| 4,304,906 | 12/1981 | Kang et al. | 536/123 |
| 4,326,053 | 4/1982 | Kang et al. | 536/123 |
| 4,342,866 | 8/1982 | Kang et al. | 536/123 |

Primary Examiner—Johnnie R. Brown
Attorney, Agent, or Firm—Gabriel Lopez; Hesna J. Pfeiffer

[57] ABSTRACT

The new heteropolysaccharide S-88, prepared by fermentation of an unnamed Pseudomonas species, ATCC 31554, has valuable properties as a thickening, suspending and stabilizing agent in aqueous systems. It is especially useful in formulating oil well drilling fluids and muds. Its chemical composition is 3.2–7% acyl groups, 11.8–18.7% glucuronic acid; and the neutral sugars mannose, glucose, and rhamnose in the approximate molar ratio 1:2:2.

3 Claims, No Drawings

HETEROPOLYSACCHARIDE S-88

CROSS-REFERENCE

This is a continuation of application Ser. No. 355,934, filed Mar. 8, 1982, now abandoned, which is a continuation-in-part of U.S. Ser. No. 256,625 filed Apr. 23, 1981, abandoned, which is a continuation-in-part of U.S. Ser. No. 73,575, filed Sept. 7, 1979, abandoned.

BACKGROUND OF THE INVENTION

Compound S-88 may be prepared by fermentation of a suitable nutrient medium with a hitherto undescribed organism, based on extensive taxonomic studies, which is an unnamed Pseudomonas species. An unrestricted permanent deposit of this organism employed in making our heteropolysaccharide was made with the American Type Culture Collection on Aug. 21, 1979 under Accession No. ATCC 31554.

Various classification keys for the genus Pseudomonas and the culture descriptions of Pseudomonas species are found in the 7th Edition of Bergey's Manual (Breed et al., (1957)) and the 8th Edition of Bergey's Manual (Doudoroff et all, (1974)), as well as by other schools in various publications; Hugh and Gilardi, 1974, Pseudomonas, *Manual of Clinical Microbiology*, 2nd ed., Lennette et al., Eds., pp. 250–269. Iizuka et al., 1963, Attempt at Grouping the Genus Pseudomonas, *J. Gen. Appl. Microbiology* 9:73–82; and Hendric et al., 1966, Identification of Certain Pseudomonas Species, Identification Methods for Microbiologists, Part A, Gibbs et al., Eds., pp. 1–7, Academic Press, New York.

These keys and descriptions were searched for a Pseudomonas species having morphological and cultural characteristics similar to those of ATCC 31554. The following considerations make the assignment of a new Pseudomonas species justified and necessary.

DESCRIPTION OF THE STRAIN

A. Characteristics of Colonial Morphology

Two types (typical and atypical) of colonies appear on both nutrient and YM agar. On nutrient agar, small translucent yellow colonies develop within 2 days at ambient temperature; diameter reaches about 1 mm in 5 days. The colonies are round, smooth-edged, and convex. Typical colonies are more glistening and the surface texture is extremely hard; entire colonies are removed if pushed by a loop; however, atypical ones do not possess such characteristics.

On YM agar, the diameter of both typical and atypical colonies are about 7-9 mm in 5 days. Both are round, smooth, convex, opaque and yellow-pigmented. Typical colonies become more umbonate-shaped and atypical ones are more flattened. Concentric rings are more significant in the case of atypical colonies. The surface of typical colonies is more slimy, and an elastic membrane is formed with prolonged incubation.

B. Characteristics of Cell Morphology

Strain S-88 is a gram-negative rod-shaped bacterium. There is no difference in the cell shape between typical and atypical strains, except with cell arrangement. Cells of a typical strain are seen in aggregation, as in a Zoogloea-like mass. On nutrient agar, the size of most cells are 0.5–0.6 by 2.0–2.5 μm; tapered at one end. Few cells are motile. Poly-β-hydroxybutyrate granules can be seen in the cells with prolonged incubation. Occasionally very long abnormal cells have been seen. Pleomorphism is common. Most cells are disintegrated within 5 days at ambient temperature.

On YM medium, cells are larger and longer (0.6–0.8 by 2.5–3.0 μm) with consistently-shaped rods. Most cells are in the arrangement of palisades. Poly-β-hydroxybutyrate granules were accumulated. Cells become very long (>5 μm) with prolonged incubation.

Flagella strains was extremely difficult because relatively few cells were flagellated, and formation of gum hindered observation of mode of flagellation. According to the methods of Iniss and Mayfield and a modified silver nitrate method, the majority of flagellated cells were monotrichously flagellated; insertion was polar and/or sub-polar.

C. Physiological and Biochemical Characteristics

Cytochrome-oxidase weak or negative; catalase positive. Organism is capable of growth at 37° C., but not at 4° C. and 41° C. No tolerance to 3% NaCl and pHs of 4 and 12. No survival at 60° C. for 30 minutes. Aerobic; acid was produced from various carbohydrates, but not gas. Nitrate may be reduced. Litmus milk was reduced, but not peptonized. $H_2S$ was not produced (lead acetate method). Phosphatase and lipase were produced. Esculin and gelatin (very weakly) were hydrolyzed, but not starch and casein. ADH, LDC, and ODC were negative. Tolerant to 0.1% triphenyltetrazolium chloride. No growth on SS, Pseudosel, or MacConkey agar media. Acid was produced on slant; no growth in the butt of TSI medium.

D. Antibiotic Susceptibility Test

The strain S-88 is susceptible to the following antibiotics:

| | |
|---|---|
| Carbenicillin | (100 μg) |
| Gentamicin | (10 μg) |
| Chlortetracycline | (5 μg) |
| Penicillin | (10 units) |
| Polymyxin B | (300 units) |
| Erythromycin | (15 μg) |
| Novobiocin | (30 μg) |
| Kanamycin | (30 μg) |
| Tetracycline | (30 μg) |
| Neomycin | (30 μg) | and not susceptible to:

| | |
|---|---|
| Streptomycin | (10 μg) |
| Colistin | (10 μg) |

E. Nutritional Characteristics

Vitamins are not required for growth. Ammonium salts serve as sole nitrogen source. At least 26 out of 123 organic compounds are utilized as a sole source of carbon and energy; most are carbohydrates.

F. G+C Content of DNA

The G+C moles % of the strain S-88 is 69.8.

G. Identification of API and OXI/FERM Tube Systems

The strain S-88 was not identified by either the API or OXI/FERM tube methods. This suggests that the organism could not be isolated from a clinical source.

H. Identification

Since strain S-88 is polar or sub-polarly monotrichously flagellated, the organism belongs to one of the members of the genus Pseudomonas, judging from the phenotypic characteristics. The G+C content of DNA (69.8 moles %) is in the range of the G+C moles % of the genus Pseudomonas.

TABLE 1

Biochemical and Other Miscellaneous Tests Employed for the Strain S-88

| Oxidase: | | Hydrolysis of: | |
|---|---|---|---|
| Kovac's | + (weak) | Gelatin | + (weak) |
| Pathotech | + (weak) | Casein | − |
| Catalase | + | Starch | − |
| OF medium: | | Tween 80 | + |
| | | Pectin | − |
| Oxidative | + | Alginate | NT |
| Fermentative | − | Cellulose | − |
| Gas from glucose | − | Chitin | − |
| H₂S production: | | DNA | NT |
| TSI | − | Esculin | + |
| from cystine | | Growth on various media: | |
| Ammonium from peptone | + | | |
| β-Galactosidase (ONPG) | − | EMB agar | + |
| Arginine dihydrolase | − | MacConkey agar | − |
| Lysine decarboxylase | − | SS agar | − |
| Ornithine decarboxylase | − | Mannitol salt agar | − |
| Tryptophan deaminase | NT | TCBS agar | − |
| Phenylalanine deaminase | − | Tinsdale tellurite blood agar | − |
| Urease | − | | |
| Indole | − | Pseudosel agar | − |
| MR test | − | Pigment production | |
| VP test | − | | |
| Nitrate reduction | − | King A medium | − |
| Nitrite reduction | − | King B medium | − |
| Denitrification | NT | Dye reaction: | |
| N₂-fixation: | | Congo red | − |
| Growth in Burk's medium | + | Nile blue | NT |
| Nitrogenase activity | NT | | |
| Malonate (oxidation) | − | | |
| Phosphatase | + | | |
| Haemolysis (sheep blood) | − | | |
| Litmus milk: | | | |
| acid, reduction only | | | |
| 3-ketolactose production | − | | |
| Survival at 60° C. for 30 min. | + | | |
| TSI: | | | |
| Slant | Acid | | |
| Butt | No Growth | | |
| Gas | − | | |
| Egg Yolk Reaction | − | | |

− = negative
+ = positive
NT = not tested

FERMENTATION CONDITIONS

Heteropolysaccharide S-88 is produced during the aerobic fermentation of suitable aqueous nutrient media under controlled conditions via the inoculation with the organism of the unnamed Pseudomonas species. The media contain sources of carbon, nitrogen and inorganic salts.

In general, carbohydrates (for example, glucose, fructose, maltose, sucrose, xylose, mannitol and the like) can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 2% and 4% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.5% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the media described in the examples are merely illustrative of the wide variety of media which may be employed, and are not intended to be limitative.

As an alternative medium, S-88 may be grown under low $Ca^{++}$ conditions, i.e., in deionized water or some other aqueous system substantially free of $Ca^{++}$ ions (i.e., less than about 4 ppm $Ca^{++}$ per 1% gum in the final fermentor broth).

The fermentation is carried out at temperatures ranging from about 25° C. to 35° C.; however, for optimum results it is preferable to conduct the fermentation at temperatures of from about 28° C. to 32° C. The pH of the nutrient media for growing the Pseudomonas culture and producing the polysaccharide S-88 can vary from about 6 to 8.

Although the polysaccharide S-88 is produced by both surface and submerged culture, it is preferred to carry out the fermentation in the submerged state.

A small scale fermentation is conveniently carried out by inoculating a suitable nutrient medium with the culture, and after transfer to a production medium permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1–2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-88 is particularly suited for the preparation of large quantities.

The product is recovered from the fermentation medium by precipitation with a suitable alcohol, such as isopropanol.

HETEROPOLYSACCHARIDE S-88

The heteropolysaccharide produced by an unnamed Pseudomonas species is composed principally of carbohydrate with 3.2–7% (calculated as O-acetyl) O-acyl groups.

The carbohydrate portion of the S-88 polysaccharide contains 11.8–18.7% glucuronic acid; and the neutral sugars mannose, glucose, and rhamnose in the approximate molar ratio 1:2:2. The ratio of terminally linked rhamnose to 1,4 linked rhamnose is 2:1. The mannose is primarily 1,4 linked.

Table II indicates specific analysis results on six fermentation samples, including triplicate analysis of two samples.

TABLE II

| | COMPOSITION OF S-88 GUM | | | | | | | | |
|---|---|---|---|---|---|---|---|---|---|
| Sample No. | Glucuronic[1] Acid (%) | Pyruvate (%) | Acetyl (%) | Neutral Sugar Components (%) | | | | | Protein (%) |
| | | | | Glu | Man | Fuc | Rha | Ara | |
| 1 | 11.8 | 0.1 | 3.2 | 33 | 22 | — | 43 | 2 | 11.8 |
| 2 | 18.7 | 0.1 | 3.2 | 38 | 22 | — | 39 | 1 | 11.9 |
| 3 | 18.0 | 0.1 | 7.0 | 38 | 24 | — | 37 | 1 | 11.5 |
| 4 | 15.8 | 0.1 | 6.6 | 35 | 27 | — | 36 | 2 | 11.7 |
| 5A | 15.1 | 0.1 | 6.1 | 33 | 25 | 3 | 37 | 2 | 12.7 |
| 5B | 15.1 | 0.1 | 6.1 | 38 | 19 | — | 41 | 2 | 12.7 |
| 5C | 15.1 | 0.1 | 6.1 | 37 | 23 | 1 | 37 | 2 | 12.7 |
| 6A | 13.7 | 0.1 | 4.9 | 36 | 22 | 1 | 40 | 1 | 14.0 |
| 6B | 13.7 | 0.1 | 4.9 | 41 | 18 | 1 | 44 | 1 | 14.0 |
| 6C | 13.7 | 0.1 | 4.9 | 38 | 20 | 0 | 41 | 1 | 14.0 |

[1]By decarboxylation

The acetyl content of 3.2–7% was determined by treating a 0.2% aqueous solution of S-88 gum with an alkaline, hydroxylamine reagent followed by treatment with an acidic ferric chloride reagent [S. Hestrin (1949) *J. Biol. Chem.* 180 pp. 249–261].

Liquid chromatography (Bio-Rad Organic Acid Analysis Column) was used to further identify the O-acyl groups. Using this technique, the O-acyl groups of S-88 have been found to be primarily O-acetyl and O-formyl, and substantially free of O-succinyl.

The neutral sugars of polysaccharide S-88 were determined by dissolving ten mg. of the product in 2 ml 2N $H_2SO_4$, and the mixture is heated at 100° C. for 4 hours. The resulting solution is cooled, neutralized with barium hydroxide and the pH is brought to 5–6 with solid carbon dioxide. The resulting precipitate of barium sulfate is removed by centrifugation and the supernatent is concentrated to a syrup under reduced pressure. The sugars in the hydrolysate are tentatively identified by gas-liquid chromatography of their aldononitrile acetate derivatives on a Hewlett-Packard Model 5750 chromotograph using 3% by weight OV-225 on 80/100 mesh Gas Chrom Q at 210° C. The sugars are identified and quantitated by comparison with authentic standards [J. K. Baird, M. J. Holroyde, and D. C. Ellwood (1973) *Carbohydr. Res.* 27 pp. 464–467].

The various neutral sugars of the polysaccharides were also characterized by use of descending paper chromatography on Whatman No. 1 chromatography paper using as the solvent the upper layer of pyridine-:ethyl acetate:water (2:5:5). Chromatograms were stained using silver nitrate dip and acid analine phthalate spray reagent. Component sugars were identified by co-chromatography with sugar standards and by the specific-color reaction with the analine phthalate reagent.

The glucuronic acid content of the polysaccharide was determined by decarboxylation with 19% hydrochloric acid and the liberated carbon dioxide was trapped in standard sodium hydroxide and determined by back titration [B. L. Browning (1967) *Methods of Wood Chemistry* II, pp. 632–633].

Paper electrophoresis was used for the separation and tentative identification of the glucuronic acid present in the neutralized acid hydrolysate described above. Aliquots of this and known glucuronic acid standards were applied to Camag electrophoresis paper No. 68-011 and electrophoresis was carried out for 2.0 hours in a pH 2.7 buffer using a Camag Model HVE electrophoresis apparatus. Chromatograms were air dried and stained with silver nitrate dip reagent to locate the glucuronic acids being separated.

The polysaccharide S-88 imparts viscosity to an aqueous medium when dissolved in water in low concentrations. Because of this, its sensitivity to shear and overall rheology, it is useful as a thickening, suspending, emulsifying, stabilizing, lubrication, film-forming, or binding agent, especially in aqueous systems. In particular, it has uses in the following applications or products: adhesives, wall-joint cements, water-retentive grouts and mortars, spackling compounds, can sealing, boiler compounds, latex creaming, welding-rod fluxes, brazing pastes, ceramic glazes and extrusions, cleaners and polishes, toys, emulsions (latex, asphalt, silicone), silver recovery, seed coatings, spray control for pesticides or herbicides, emulsifiable concentrated and flowable pesticides and herbicides, tobacco binders, water-based inks lithographic fountain solutions, leather finishes, hydro-mulching and hydro-seeding, textile printing and finishing, wet-end paper additives, wet-end paper retention and formation aid, anti-stick compounds, mold-release agents, liquid resins, slurry and packaged explosives, petroleum and water-well drilling muds, petroleum workover and completion fluids, petroleum stimulation fluids, cosmetics, pharmaceutical suspensions and emulsions.

Also this gum has utility in food systems such as jellies and other high sugar systems, beverages including citric acid based drinks, dairy products including ice cream and yogurt, salad dressings, dry mixes, icings, and glazes, syrups, puddings, farinaceous foods, canned and retorted foods, and bakery fillings.

A particularly valuable utility is in the field of petroleum and water-well drilling muds. More detailed examples illustrating this preferred use are found, infra.

Although S-88 gum possesses a general viscosity-imparting property, its particular profile of solution properties is a distinctive characteristic which enables it to be distinguished over other heteropolysaccharides.

In its dry form, the gum has a solids content of 85–90%; its most useful mesh size is 100% through 40 mesh, with no more than 30% through 325 mesh. It has a 1200–2500 cP at 1%, Brookfield, 60 rpm, and the following dial readings at 0.4% concentration in 2% KCl tap water, Fann 35 (F=02): 600 rpm>120; 300 rpm>92; 200 rpm>76; 100 rpm>70; 6 rpm>32; and 3 rpm>28.

The gum further has excellent heat stability, and no viscosity loss upon autoclaving at 121° C. and 15 psi for 15–20 minutes. It produces a firm gel with 15% NaOH and incubation at 80° C. for two hours. It is incompatible with saturated $CaCl_2$, ammonium polyphosphate, and 60% $NH_4NO_3$.

In addition, the gum has the following profile of properties:

1. Viscosity and Shear
   A. Brookfield
      1. 1.0%    60 rpm    1520 cPs
                 6 rpm     11,600 cPs
                 Spindle No. 3
      2. 0.1% (UL adapter)[a]    29.5 cPs
      3. 0.5% Wells-Brookfield   474 cPs
         @ 9.6 sec$^{-1}$
   B. Shear[b]
      1. n @ 1.92 sec$^{-1}$    8512 cPs
      2. n @ 9.6 sec$^{-1}$     2342 cPs
      3. n @ 76.8 sec$^{-1}$    320 cPs
      4. n @ 384 sec$^{-1}$     64 cPs
      5. n @ 384$^2$ sec$^{-1}$  64 cPs
      6. n @ 9.6 sec$^{-1}$     1958 cPs
   C. 40° F. Storage
      1450 cPs, No. 3 spindle @ 60 rpm, no gelation, chunky flow.
2. Acid, Base, Heat Stability
   A. Stability
      1. Acetic acid plus heat -
         a. initial n: 1620 cPs
         b. final n: 2450 cPs
         c. % change: +51% (gel-like)
      2. 10% HCl plus heat -
         a. initial n: Ppt cPs
         b. final n: Ppt cPs
         c. % change: Ppt %
      3. 15% NaOH plus heat-
         a. initial n: 1869 cPs
         b. final n: Gel cPs
      4. Heat only -
         a. initial n: 2061 cPs
         b. final n: 2266 cPs
         c. % change: +10%
   B. pH Effect
      1. 5% Acetic Acid    2.69 pH    1741 cPs[c]
      2. 5% $NH_4OH$       10.99 pH   1741 cPs[c]
      3. S-88 solution is stable over the pH range 1.25–12.3.
3. Salt and Dye Compatibility
   A. Salt
      1. $CaCl_2$ (saturated)         Precipitate
      2. Amm. polyphosphate           Precipitate
      3. 60% $NH_4NO_3$               Precipitate
      4. 1% $Al_2(SO_4)_3 \cdot 18H_2O$   Compatible
      5. 1% $CaCl_2 \cdot 2H_2O$      Compatible
      6. 1% KCl                       Compatible
      7. 0.1% KCl                     2214 cPs[c]
      8. 2.5% KCl                     922 cPs[c]
   B. Dyes
      1. Milling Green                Compatible
      2. Methylene Blue               Precipitate
4. Texture/Flow Properties
   Chunky, non-continuous flow, high viscosity, gel-like, gummy to the touch.
5. Synergism and Enzymes[c]

|   |          | 1% n      | 0 hr n of mixture | 2 hr n of mixture |
|---|----------|-----------|-------------------|-------------------|
| A.| Guar     | 1600 cPs  | 1702 cPs          | 1741 cPs          |
| B.| H.P. Guar| 1715 cPs  | 1741 cPs          | 1741 cPs          |
| C.| CMC      | 832 cPs   | 1088 cPs          | 1665 cPs          |
| D.| HEC      | 602 cPs   | 1229 cPs          | 998 cPs           |
| E.| MAS 1-1  | 2253 cPs  |                   |                   |

|   |          | Expected Viscosity | Synergism |
|---|----------|--------------------|-----------|
| A.| Guar     | 1900 cPs           | None      |
| B.| H.P. Guar| 1975 cPs           | None      |
| C.| CMC      | 1375 cPs           | +21       |
| D.| HEC      | 1175 cPs           | None      |

6. Milk Reactivity
   A. Dispersion: Poor-small granular precipitate
   B. Whey off: 1st day
7. Film Formation
   Gum pulls down unevenly, film formed, uneven consistency, slightly plastic, brittle.

[a] Viscosity measured on a Brookfield Model LVF at 6 rpm with the No. 1 spindle and a UL adapter.
[b] All measurements made on a Wells-Brookfield micro-viscometer Model RVt-c/p.
[c] Viscosity measured on a Wells-Brookfield micro-viscometer Model RVT-c/p at 9.6 sec$^{-1}$.

Cross-linking of S-88 with various polyvalent ions was tested by preparing 0.4% S-88 solutions in 2% KCl tap water. To 200 ml of these solutions were added, respectively: (1) 1.0 g chrome alum crystal dissolved in 5 ml $H_2O$; (2) 1.0 g aluminum sulfate dissolved in 5 ml $H_2O$; (3) 1.5 ml Zircomplex ® (Manchem, Manchester); (4) 1.5 ml Tysor LA (Dupont); and (5) 0.5 g $FeCl_3$ dissolved in 5 ml $H_2O$. These solutions were allowed to stand for 15 min., then checked for cross-linking. If no cross-linking was observed the pH was raised to 9.0 using 15% NaOH and the solutions re-checked. Fresh solutions were prepared and the pHs adjusted with either 15% NaOH or 15 HCl to 4, 7, and 9 and checked for cross-linking after 15 min. S-88 did not cross-link under any of these conditions.

EXAMPLE 1

Fermentation Procedure for Producing Heteropolysaccharide S-88

A. Culture Maintenance

The unnamed Pseudomonas organism, ATCC 31554, grows quite well on NA agar at an incubation temperature of 30° C. This organism produces a yellow carotenoid pigment. The colonies on NA are small (only 1–3 mm) by 48 hrs., are convex, and have a gelatinous texture. The typical colony has a tendency to stick tenaciously to the agar surface. Occasionally, a morphological variant may develop which is easy to spot on NA. The variant has a flat colony and does not stick tenaciously to the agar surface. This variant was found to have a decreased activity of S-88 gum production.

B. Seed Preparation

Flask seeds are prepared in YM broth incubated at 30° C.

In this medium the culture will typically give flocculant-type growth followed by viscosity increases with a granular-type appearance. The YM seeds are then used at 24–30 hrs. to inoculate seed medium which is the same as final fermentor medium, except that the phosphate concentration is increased to 0.5%. One-gallon fermentors are used as seed vessels for the 20 L and 70 L fermentors.

C. Final Fermentor Medium

The following medium gives acceptable results in both 20 L and 70 L fermentors.

| | |
|---|---|
| Glucose | 3.0% |
| K$_2$HPO$_4$ | 0.05% |
| AMP | 0.05% |
| NH$_4$NO$_3$ | 0.09% |
| MgSO$_4$.7H$_2$O | 0.01% |
| Fe$^{++}$ | 1 ppm |
| HoLe salts | 1 ml/L |

An agitation rate set at 500 rpm in both the 20 L and 70 L fermentors is desirable. Fermentation times can range from 45–70 hrs. with beer viscosity ranging from 3000 cps to 5000 cps. Conversion efficiencies vary from 31–52% with 3% glucose. Small amounts of commercially available antifoam agent can be used.

Gram stains made from S-88 fermentation beer showed gram-negative cells approximately 1.25μ×2.5μ in size with dark staining polar bodies.

HoLe salts are a trace element solution containing tartrate, magnesium molybdate, CoCl$_3$, ZnCl$_2$, CuCl$_2$, boric acid, manganese chloride and ferrous sulfate.

When a low calcium product is desired, a 30 L fermentor medium is as follows:

| 30L Fermentor Medium for Low-Calcium Deionized water | |
|---|---|
| Glucose | 3.0% |
| K$_2$HPO$_4$ | 0.05% |
| AMP | 0.05% |
| MgSO$_4$.7H$_2$O | 0.02% |
| NH$_4$NO$_3$ | 0.09% |
| Yeast extract | 0.01% |
| HoLe salts | 40 ml |
| Vitamin mix | 25 ml |
| Fe$^{++}$ | 1 ppm |
| Ca$^{++}$ | 2 ppm |

The vitamin mixture is a mixture of 1 μ/ml each of thiamine, cyanocobalamin, pantothenate, riboflavin, nicotinic acid, choline, and pyridoxamine; 0.05 μ/ml folic acid and p-aminobenzoic acid; and 0.005 μ/ml biotin.

D. Recovery

Fermentation beer is pasteurized at 167° F. for 10–15 min. Due to the excellent heat stability exhibited by this product, higher pasteurization temperatures with shorter holding times should be acceptable. Good fibers are typically produced under precipitation conditions giving 58–60% spent IPA.

E. Drying

All product recovered thus far has been dried at 50°–55° C. for up to one hour in a forced-air tray dryer.

The properties of S-88 gum produced during these fermentation conditions have been given above.

When the low calcium S-88 gum is prepared, it shows a similar chemical analysis and property profile to S-88, but has an unusual response in NaCl solution. Although the initial viscosity in 0% salt is slightly low, a stable viscosity is maintained up to 6%, see Table III.

TABLE III

| Salt Response: NaCl | | | | | | | | |
|---|---|---|---|---|---|---|---|---|
| NaCl Concentration, wt. % | | | | | | | | |
| | 0 | 2 | 4 | 6 | 8 | 10 | 15 | 20 |
| 600$^a$ | 13.4 | 14.2 | 14.8 | 13.8 | 11.4 | 10.2 | 9.5 | 9.0 |
| 300$^a$ | 20.1 | 21.4 | 22.0 | 20.6 | 20.2 | 19.7 | 19.4 | 19.0 |
| 200$^a$ | 26.0 | 26.1 | 27.1 | 25.4 | 24.3 | 24.3 | 23.8 | 23.6 |
| 100$^a$ | 41.7 | 42.0 | 42.3 | 41.2 | 40.6 | 39.6 | 39.1 | 38.5 |
| 6$^a$ | 332 | 339 | 342 | 326 | 289 | 276 | 254 | 232 |
| 3$^a$ | 578 | 577 | 586 | 563 | 510 | 482 | 441 | 410 |

$^a$viscosity, cP at Fann 35 rpm

FORMULATIONS USING S-88

As noted above, S-88 gum, both in regular or low calcium form, can be used in fresh- or salt-water drilling muds.

A typical formulation for a fresh-water mud is as follows:

| | |
|---|---|
| S-88 | 1.0 lbs. |
| Bentonite | 10.0 lbs. |
| Fresh Water | 1.0 bbl |

| Fann Viscosity Data: | | | | | | |
|---|---|---|---|---|---|---|
| Speed (rpm) | 3 | 6 | 100 | 200 | 300 | 600 |
| Dial Reading | 7.6 | 7.9 | 16.8 | 21.5 | 25.6 | 35.3 | pH = 8.3; API Filtrate = 12.0 ml

Another formula, for a salt-water mud, is:

| | |
|---|---|
| S-88 | 1.0 lb |
| Sea Water | 1.0 bbl |

| Fann Viscosity Data: | | | | | | |
|---|---|---|---|---|---|---|
| Speed (rpm) | 3 | 6 | 100 | 200 | 300 | 600 |
| Dial Reading | 2.8 | 3.2 | 9.0 | 12.8 | 15.6 | 23.6 | pH = 7.2

EXAMPLE 2

Methylation Analysis

Samples of S-88 have shown analyses indicated on Table IV. A partial structural determination was performed by methylation of the component sugars. The methylated sugars were separated by gas chromatography, and then analyzed on a mass spectrometer. This analysis demonstrated that the ratio of terminally linked to 1,4 linked rhamnose sugars is 2:1 and that the mannose is primarily 1,4 linked.

TABLE IV

| Composition of S-88 | | | | | | | |
|---|---|---|---|---|---|---|---|
| GluA (%) | Neutral Sugars[1] | | | | | Pyruvic Acid (%) | O—Acyl[2] (%) |
| | Glu | Man | Rha | Rib | Ara | | |
| 11.8–18.7 | 33–42 | 13–27 | 36–44 | tr | tr | 0 | 3.2–7.0 |

[1]% of total neutral sugars
[2]Calculated as O—Acetyl

Approximately 40 mg dialyzed and freeze dried sample of S-88 was weighed (dry) into 100 ml serum bottles before inserting rubber serum caps. Then approximately 40 ml of dimethyl sulfoxide (DMSO) (redistilled and dried over 4A molecular sieves) was added. The sample was dissolved by heating in a sonic bath for ca. 20 hr. at ca. 50° C. while the vial was continuously flushed with dry nitrogen. To the vial was added 20 ml anion solution made from DMSO and NaH (2.5 g/50 ml DMSO). The vial was placed in sonic water bath for ca. 30 min. before leaving at room temperature overnight. The solution was cooled and then 20 ml CH$_3$I was added via a syringe. After stirring for at least one hour, the excess CH$_3$I was rotovaped off before dialysis (DI water) and concentrating to dryness (rotovap).

Hydrolysis of methylated gums and derivatation of methyl sugars

The sample was hydrolyzed by a two-step procedure using 90% formic acid/0.13M H$_2$SO$_4$. The resulting sugars were reduced with NaBH$_4$ and the resulting alditols were acetylated with acetic anhydride/pyridine (1:1) at 100° C.

Gas Chromatography

The methyl sugars, as their alditol acetates, were separated by gas chromatography using either SP-2330 or OV-225 columns. The following conditions were used:

| 3% SP-2330 (on 100/120 Supelcoport, 2 mm × 6 ft) | |
|---|---|
| Column temp. | isothermal at 190° C. |
| Injection port | 215° C. |
| FID Temp | 350° C. |
| Oven Max | 250° C. |
| Chart Speed | 0.50 |
| Attenuation | 8 |
| FID Signal | A-B |
| Slope Sensitivity | 0.50 |
| Area Rejection | 1 |
| Flow A | 40 |
| Flow B | 40 |

3% OV-225 (on 80/100 Supelcoport, 2 mm × 4 ft)
Column temp - isothermal at 170° C. (other conditions as above)

The same columns and flow rates were used with GC/Mass Spectrometer. The retention times (RT) on the Hewlett Packard Model 5830A gas chromatograph were found to be much more reproducible than on the Hewlett Packard Model 5992A GC/Mass spectrometer. The identities were deduced by looking at both RT's and mass fragmentation patterns. With the columns used it is not possible to determine if the 2,6 Me$_2$ hexose found in S-88 is 2,6 Me$_2$ glucose or 2,6 Me$_2$ mannose. Based on the relative amounts of glucose and mannose expected from alditol acetate analysis of neutral sugars and based on the amounts of other methyl sugars found (Table V), S-88 probably contains 2,6 Me$_2$ glucose. However, these data are shown in Table V as 2,6 Glucose/Mannose.

Based on the methylation data, the amounts of the various linkages are shown in Table VI.

TABLE V

| Relative Amounts of Methyl Sugars | | |
|---|---|---|
| | S-88 (Wt. %) | Linkage |
| 2,3,4 Me$_3$ Rha | 36.4 | Terminal |
| 2,3 Me$_2$ Rha | 22.4 | 1,4 |
| 2,4,6 Me$_3$ Glu | 7.4 | 1,3 |
| 2,3,6 Me$_3$ Glu | 4.2 | 1,4 |
| 2,3,6 Me$_3$ Man | 15.7 | 1,4 |
| 2,6 Me$_2$Glu/Man | 13.8 | 1,3,4 |

TABLE VI

| Types and Amounts of GLYCOSIDIC LINKAGES | |
|---|---|
| Linkage | Moles |
| Term. Rha | 2 |
| 1,4 Rha | 1 |
| 1,3 Glu | — |
| 1,4 Man | 1 |
| 1,3,4 Glu/Man | 1 |

Fragments released by mild acid were also anaylzed. A sample of S-88 was hydrolyzed under mild conditions (1.0N H$_2$SO$_4$, 100° C.) and the resulting fragments were separated by paper chromatography (pyridine:ethyl acetate:water (2:5:5), upper phase). Based on chromatograms developed with silver nitrate, S-88 was found to give spots corresponding in mobility to the reducing sugars rhamnose, mannose, glucose, glucuronic acid and an additional but unidentified slow moving component (R$_{Glc}$=0.56).

What is claimed is:

1. Heteropolysaccharide S-88, which is principally carbohydrate, comprising 3–7% (calculated as O-acetyl) O-acyl groups, said O-acyl groups being primarily O-acetyl and O-formyl and substantially free of O-succinyl, 11.8–18.7% glucuronic acid, and the neutral sugars mannose, glucose, and rhamnose in the approximate molar ratio 1:2:2, wherein the ratio of terminally linked rhamnose to 1,4 linked rhamnose is 2:1 and the mannose is principally 1,4 linked.

2. The heteropolysaccharide of claim 1 prepared by fermentation under controlled conditions of culture ATCC 31554, a Pseudomonas species.

3. The heteropolysaccharide of claim 2 prepared in a fermentation medium substantially free of Ca$^{++}$ ions.

* * * * *